United States Patent
Xu et al.

(10) Patent No.: US 12,082,791 B2
(45) Date of Patent: Sep. 10, 2024

(54) MULTI-PURPOSE FLEXIBLE SURGICAL TOOL SYSTEM

(71) Applicant: Beijing Surgerii Robotics Company Limited, Beijing (CN)

(72) Inventors: Kai Xu, Shanghai (CN); Jiangran Zhao, Shanghai (CN); Shu'an Zhang, Shanghai (CN); Jing Zhu, Shanghai (CN); Yitang Ren, Shanghai (CN); Linhui Niu, Shanghai (CN); Tianlai Dong, Shanghai (CN); Jingxi Lu, Shanghai (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 788 days.

(21) Appl. No.: 16/961,210

(22) PCT Filed: Jan. 8, 2019

(86) PCT No.: PCT/CN2019/070890
§ 371 (c)(1),
(2) Date: Jul. 9, 2020

(87) PCT Pub. No.: WO2019/137380
PCT Pub. Date: Jul. 18, 2019

(65) Prior Publication Data
US 2020/0405279 A1  Dec. 31, 2020

(30) Foreign Application Priority Data
Jan. 10, 2018  (CN) .......................... 201810022341.7
Jan. 10, 2018  (CN) .......................... 201810023059.0

(51) Int. Cl.
*A61B 17/00*  (2006.01)
*A61B 1/005*  (2006.01)
(Continued)

(52) U.S. Cl.
CPC ...... *A61B 17/00234* (2013.01); *A61B 1/0055* (2013.01); *A61B 1/0057* (2013.01);
(Continued)

(58) Field of Classification Search
CPC .......... A61B 17/00234; A61B 17/3423; A61B 2017/00314; A61B 2017/00327; A61B 2034/301; A61B 1/04; A61B 1/06
See application file for complete search history.

(56) References Cited

U.S. PATENT DOCUMENTS 9,814,480 B2   11/2017  Tadano et al.
2006/0112795 A1  6/2006  Chang
(Continued)

FOREIGN PATENT DOCUMENTS

CN   103356287 A   10/2013
CN   106236269 A   12/2016
(Continued)

OTHER PUBLICATIONS

European Patent Office, Extended European Search Report Issued in Application No. 19738935.6, May 26, 2021, Germany, 10 pages.
(Continued)

*Primary Examiner* — Brooke Labranche
(74) *Attorney, Agent, or Firm* — McCoy Russell LLP

(57) ABSTRACT

The invention relates to a multi-purpose flexible surgical instrument system including a flexible surgical instrument, which includes a flexible continuum structure and a transmission driving unit. The flexible continuum structure includes a distal structure, a proximal structure, and a connecting body; the proximal structure includes a first distal segment and a second distal segment; the transmission drive unit is coupled to the first distal segment to drive the first distal segment to perform a bending motion; the second distal segment is coupled to the proximal structure via the
(Continued)

connecting body, and the transmission driving unit is further coupled to the proximal structure to drive the proximal structure perform a bending motion, thereby indirectly drive the second distal segment to perform a bending motion.

34 Claims, 13 Drawing Sheets

(51) Int. Cl.
*A61B 34/00* (2016.01)
*A61B 1/04* (2006.01)
*A61B 1/06* (2006.01)
*A61B 17/29* (2006.01)
*A61B 17/34* (2006.01)
*A61B 34/30* (2016.01)

(52) U.S. Cl.
CPC ............... *A61B 34/71* (2016.02); *A61B 1/04* (2013.01); *A61B 1/06* (2013.01); *A61B 2017/00314* (2013.01); *A61B 2017/00327* (2013.01); *A61B 2017/00398* (2013.01); *A61B 17/29* (2013.01); *A61B 17/3423* (2013.01); *A61B 2034/301* (2016.02)

(56) References Cited

U.S. PATENT DOCUMENTS

| | | |
|---|---|---|
| 2006/0199999 A1 | 9/2006 | Ikeda et al. |
| 2015/0080908 A1 | 3/2015 | Lathrop et al. |

FOREIGN PATENT DOCUMENTS

| | | |
|---|---|---|
| CN | 106308934 A | 1/2017 |
| CN | 106308935 A | 1/2017 |
| CN | 106308936 A | 1/2017 |
| CN | 106344157 A | 1/2017 |
| CN | 106361432 A | 2/2017 |
| CN | 106473810 A | 3/2017 |
| CN | 106510849 A | 3/2017 |
| CN | 106562806 A | 4/2017 |
| CN | 107997824 A | 5/2018 |
| CN | 108245254 A | 7/2018 |
| KR | 20110032444 A | 3/2011 |
| WO | 2009094670 A1 | 7/2009 |

OTHER PUBLICATIONS

European Patent Office, Partial Supplementary European Search Report Issued in Application No. 19738935.6, Feb. 26, 2021, Germany, 15 pages.

ISA State Intellectual Property Office of the People's Republic of China, International Search Report Issued in Application No. PCT/CN2019/070890, Apr. 3, 2019, WIPO, 5 pages.

MULTI-PURPOSE FLEXIBLE SURGICAL TOOL SYSTEM

CROSS-REFERENCE TO RELATED APPLICATIONS

The present application is a U.S. National Phase of International Patent Application No. PCT/CN2019/070890 entitled "MULTI-PURPOSE FLEXIBLE SURGICAL TOOL SYSTEM," filed on Jan. 8, 2019. International Patent Application Serial No. PCT/CN2019/070890 claims priority to Chinese Patent Application No. 201810023059.0, filed on Jan. 10, 2018 and a Chinese Patent Application No. 201810022341.7, filed on Jan. 10, 2018. The entire contents of each of the above-referenced applications which are hereby incorporated by reference in its entirety.

TECHNICAL FIELD

The present application belongs to the field of medical instrument, and specifically relates to a multi-purpose flexible surgical instrument system.

BACKGROUND AND SUMMARY

Multi-port laparoscopic minimally invasive surgery has occupied an important position in surgery because of it having small wound and rapid postoperative recovery. The existing da Vinci surgical robot of the Intuitive Surgical, Inc. assists doctors in implementing the multi-port laparoscopic minimally invasive surgery and has achieved great commercial success.

For the minimally invasive surgery, after the multi-port laparoscopic surgery, single-port laparoscopic surgery and natural orifice transluminal non-invasive surgery have been further developed and have less trauma to the patient and higher postoperative outcomes. However, in the single-port laparoscopic surgery and the natural orifice transluminal non-invasive surgery, all surgical instruments including a visual illumination module and a surgical manipulator have access to the surgical site through a single channel, which is extremely stringent for the preparation of the surgical instruments. A distal structure of an existing surgical instrument is mainly of multiple rods articulated in series, and is driven by a pulling force from a wire rope, so that the surgical instrument can bend at an articulated joint. Since the wire rope has to be continuously tensioned by a pulley, this driving method can hardly lead to further miniaturization of the surgical instrument, and also further improvement of the moving performance of the instrument.

The Intuitive Surgical, Inc. recently launches a Da Vinci Single-Site (Da Vinci SS) surgical robot, in which the original rigid surgical instrument is modified into a semi-rigid surgical instrument and a pre-bent sleeve is additionally provided so as to improve the moving performance of the surgical instrument to a certain extent.

The present application discloses multi-purpose surgical instrument system, which includes a flexible surgical instrument; the flexible surgical instrument includes a flexible continuum structure and a transmission driving unit, the flexible continuum structure includes a distal structure, a proximal structure and a connecting body, and the distal structure includes a first distal segment and a second distal segment; the transmission driving unit is coupled to the first distal segment to drive the first distal segment to perform a bending motion, the second distal segment is coupled to the proximal structure via the connecting body, and the transmission driving unit is also associated with the proximal structure to drive the proximal structure to perform a bending motion, so as to indirectly drive the second distal segment to perform a bending motion.

DETAILED DESCRIPTION

Figure 1:
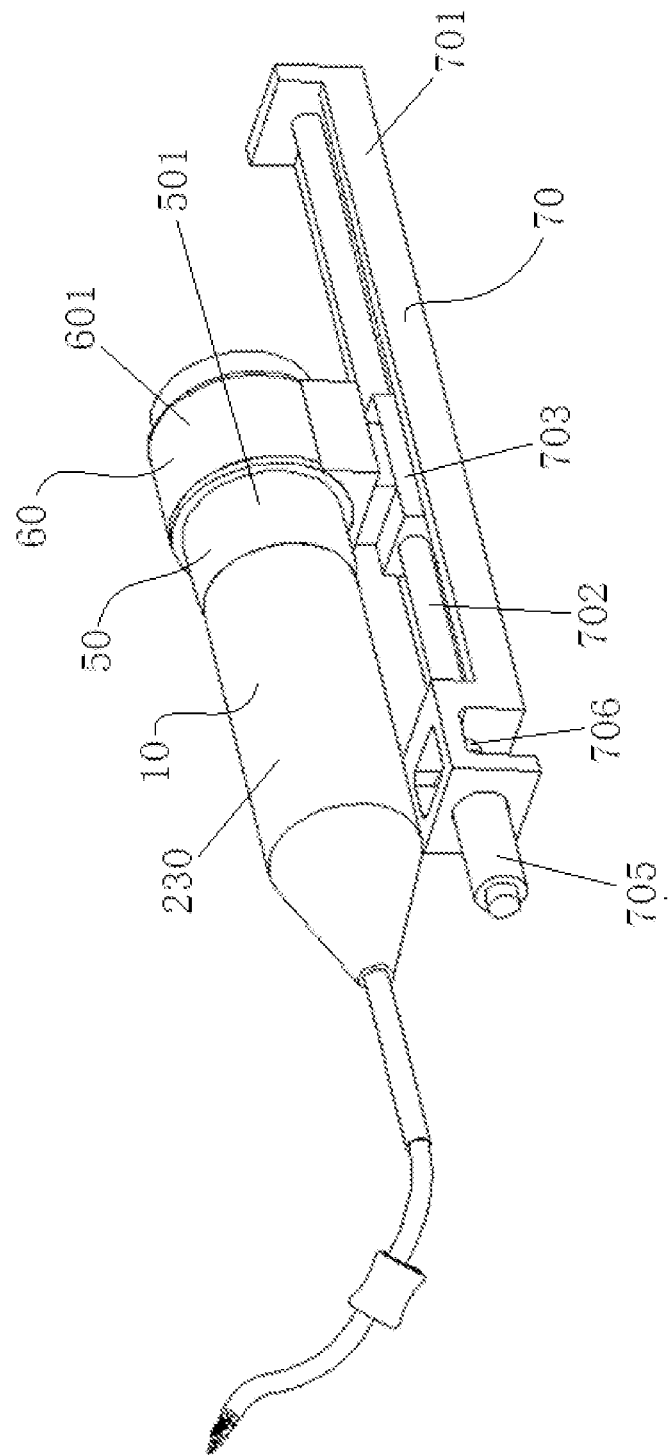
FIG. 1 is an overall structural diagram of the flexible surgical instrument according to an embodiment of the present invention.
Figure 2:
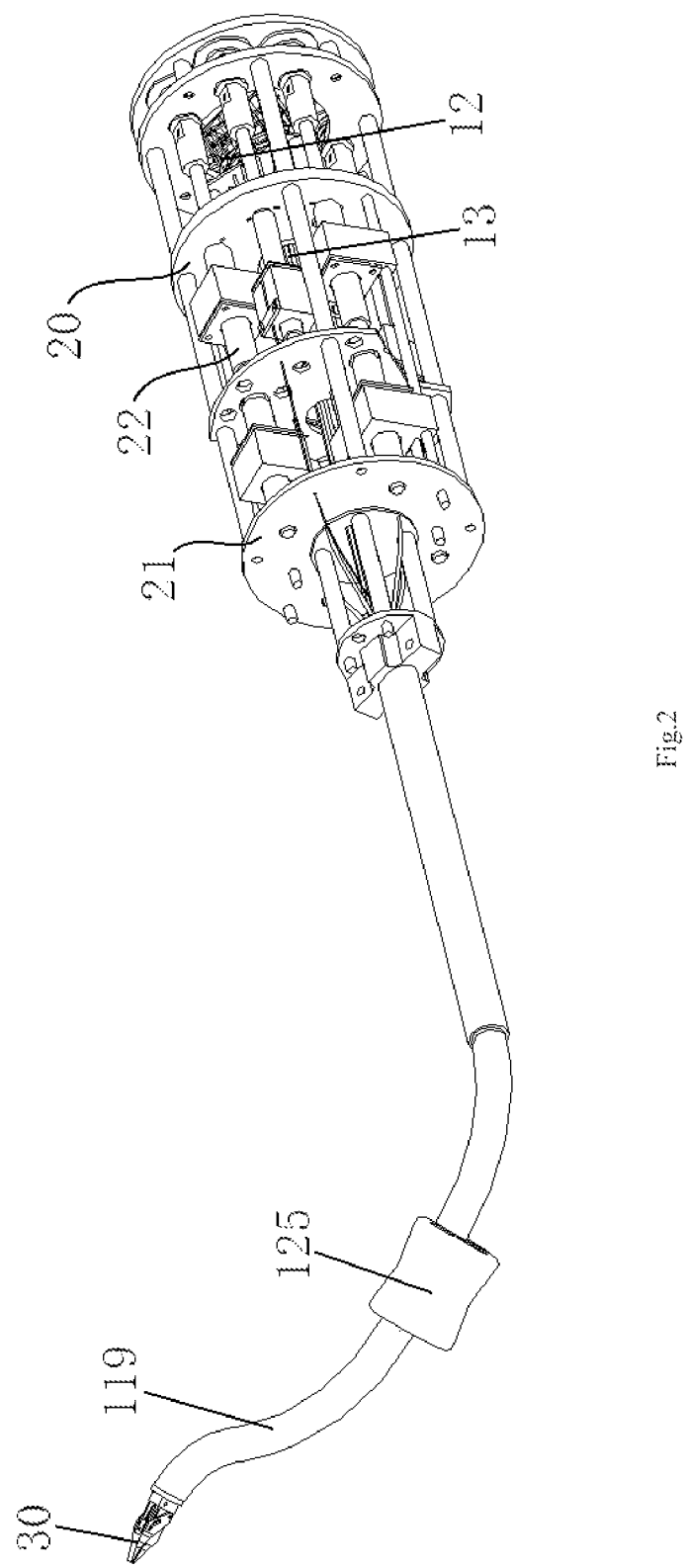
FIG. 2 is a structural diagram of the flexible surgical instrument according to an embodiment of the present invention, with the housing removed.

Embodiments of the present invention is to be described in a clear, detailed way below in conjunction with the accompanying drawings of the embodiments, and obviously, the embodiments described are just a portion of the embodiments of the present application, instead of all the embodiments. Based on the embodiments of the present application, any other embodiments obtained by one skilled in the art without creative efforts all belong to the protective scope of the present application.

As shown in FIGS. 1-4, the present invention includes a flexible surgical instrument 10, a sterile barrier 50, a multi-motor assembly unit 60, and a linear actuation module 70. The flexible surgical instrument 10 includes a flexible continuum structure and a transmission driving unit 20. The flexible continuum includes a distal structure 11, a proximal structure 12 and a connecting body 13. The distal structure 11 includes a first distal segment 14 and a second distal segment 15. The transmission driving unit 20 is coupled to the first distal segment 14 to drive the first distal segment 14 to perform a bending motion. The second distal segment 15 is coupled to the proximal structure 12 via the connecting body 13. The transmission driving unit 20 is also coupled to the proximal structure 12, to drive the proximal structure 12 to perform a bending motion, so as to indirectly drive the second distal segment 15 to perform a bending motion. The multi-motor assembly unit 60 is connected to the flexible surgical instrument 10 via the sterile barrier 50, so as to provide driving force to the transmission driving unit 20. The output end of the linear actuation module 70 is connected to the multi-motor assembly unit 60 for driving the multi-motor assembly unit 60 and the flexible surgical instrument 10 to achieve a linear feed motion.

Furtherly, the first distal segment 14 includes a first distal spacing disk 141, a first distal fixation disk 142 and first distal structural backbones 143. The first distal structural backbones 143 are connected at one end to the transmission driving unit 20, and are securely connected at the other end to the first distal fixation disk 142 after through the connecting body 13 and the first distal spacing disk(s) 141 in sequence. The second distal segment 15 includes a second distal spacing disk 151, a second distal fixation disk 152 and second distal structural backbones 153. The proximal structure 12 includes a proximal spacing disk 121, a proximal fixation disk 122 and proximal structural backbones 123. The second distal structural backbones 153 are securely connected, in one-to-one correspondence, to the proximal structural backbones 123, or they are one same structural backbones, and the structural backbones are securely connected at one end to the proximal fixation disk 122, and securely connected at the other end to the second distal fixation disk 152 after through the proximal spacing disks 121, the connecting body 13, the first distal spacing disks 141, the first distal fixation disk 142, and the second distal spacing disks 152 in sequence.

The transmission driving unit 20 includes a fundamental frame 21 and a linear motion mechanism 22 provided in the fundamental frame 21 for transferring rotary motion input to a linear motion output. There may be a plurality of linear motion mechanisms 22. Wherein, a portion of the linear motion mechanisms 22 are connected at output ends thereof to the first distal structural backbones 143, another portion of the linear motion mechanisms 22 are connected at output ends thereof to one end of a driving backbone 124. The other end of the driving backbone 124 is securely connected to the proximal fixation disk 122 after through the proximal spacing disks 121 in sequence.

Figure 5:
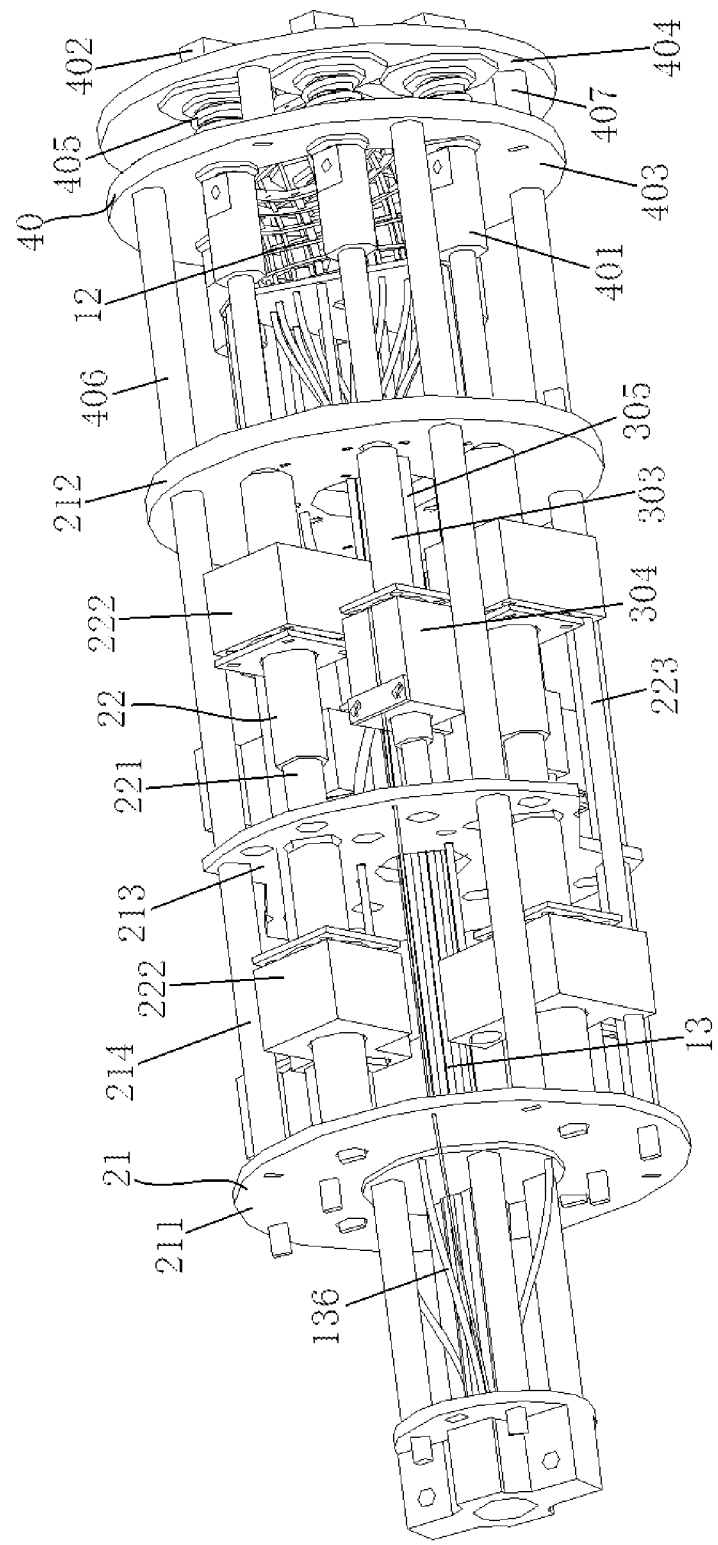
FIG. 5 is a structural diagram of the transmission driving unit according to an embodiment of the present invention.

As shown in FIG. 5, the fundamental frame 21 includes a first support plate 211 and a second support plate 212 in spaced apart arrangement. The linear motion mechanism 22 includes a double-head threaded rod 221 rotatably connected to the first support plate 211 and the second support plate 212. Two threaded segments of the double-head threaded rod 221 are respectively engaged with a threaded sliding block 222. The threaded sliding blocks 222 are slidably connected to a guide rod 223 fixedly provided between the first support plate 211 and the second support plate 212. Thus, the threaded sliding blocks 222 form the output ends of the linear motion mechanism 22. The threads on the two threaded segments of the double-head threaded rod 221 are opposite to each other. Thus, as the double-head threaded rod 221 rotates, the two threaded sliding blocks 222 on the double-head threaded rod 221 linearly move along opposite directions in identical velocity. Therefore, the two threaded sliding blocks 222 respectively drive the first distal structural backbones 143 and the driving backbone 124 to linearly move along the guide rod 223 in opposite directions with identical velocity, so that the first distal backbones 143 and the driving backbone 124 is pushed or pulled, then bending of the first distal segment 14 and the proximal structure 12 in any direction is achieved.

Figure 9:
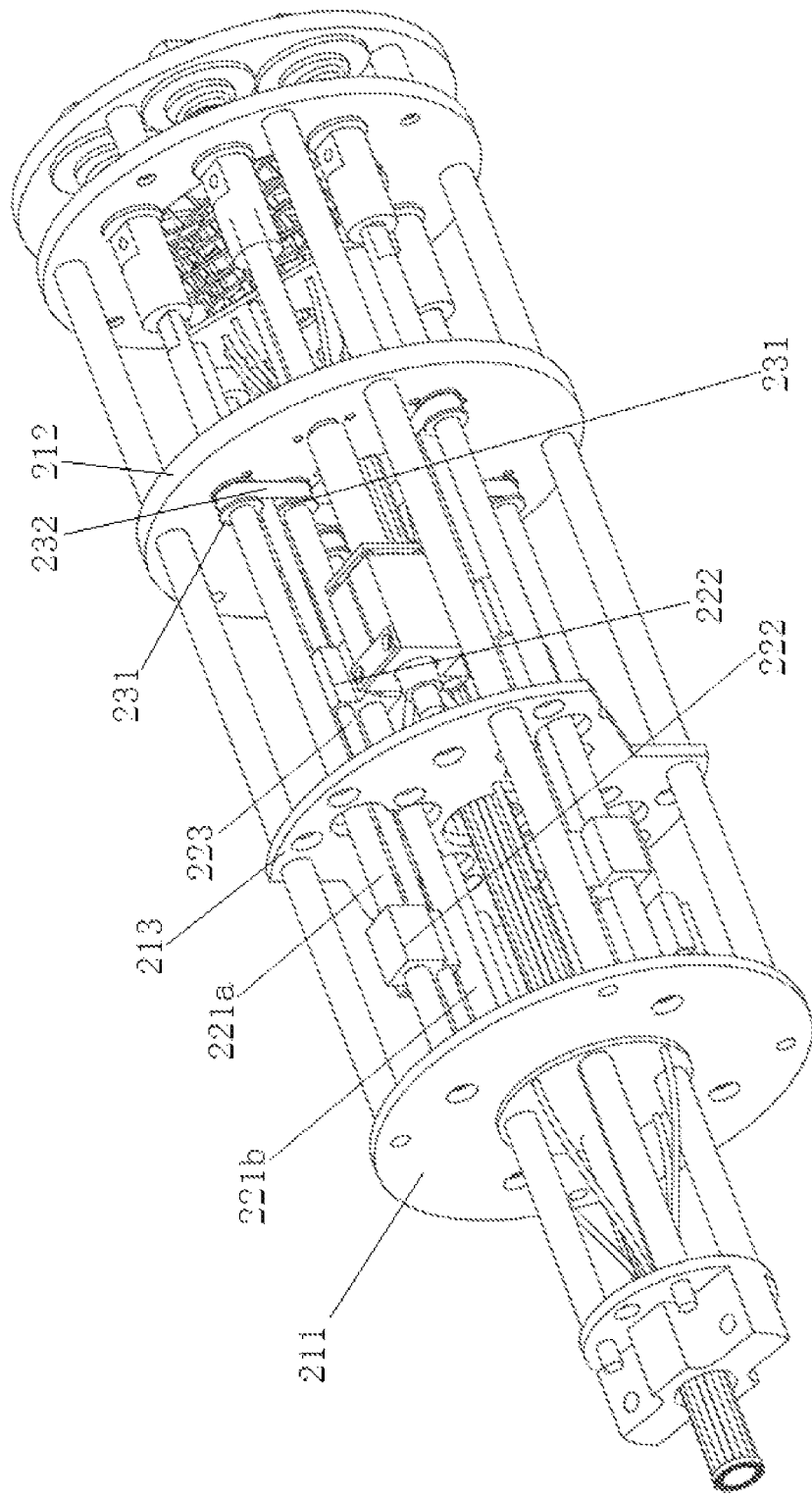
FIG. 9 is a structural diagram of the transmission driving unit according to another embodiment of the present invention.

As shown in FIG. 9, another embodiment of the present invention further provides a linear motion mechanism 22. Specifically, this linear motion mechanism 22 includes a driving screw 221a and a driven screw 221b rotatably connected between the first support plate 211 and the second support plate 212. The driving screw 221a and the driven screw 221b are respectively connected with a threaded sliding block 222 by thread engagement. The threaded sliding blocks 222 are slidably connected to a guide rod 223 fixedly provided between the first support plate 211 and the second support plate 212. The driving screw 221a and the driven screw 221b are respectively firmly sleeved by a synchronism pulley 231. The two synchronism pulleys are connected to each other by a synchronism belt 232. The threads of the driving screw 221a and the driven screw 221b are opposite to each other. When the driving screw 221a rotates, the threaded sliding block 222 on the driving screw 221a and the threaded sliding block 222 on the driven screw 221b linearly move in opposite directions with identical velocity.

In a preferred embodiment, the output ends of two linear motion mechanism 22 are connected to the first distal structural backbones 143, thus degrees of bending freedom of the first distal segment 14 in two directions are achieved; output ends of additional two linear motion mechanism 22 are connected to the driving backbone 124, thus degrees of bending freedom of bending of the proximal structure 12 in two directions. As the proximal structure 12 bends in a certain direction, the second distal segment 15 will bend in an opposite direction in a certain proportional relationship (determined by the distribution radius of the proximal structural backbones 124 and the second distal structural backbones 153 together).

Furtherly, the first support plate 211 and the second support plate 212 are fixedly connected by a support rod. A connecting plate 213 is provided between the first support plate 211 and the second support plate 212, and also fixedly connected by the support rod. A positioning sleeve 214 is sleeved on the support rod, for positioning the connecting plate 213, the first support plate 211 and the second support plate 212. The double-head threaded rod 221 extends through the connecting plate 213 with a gap between the double-head threaded rod 221 and the connecting plate 213, and the connecting plate 213 spaces the two threaded segments of the double-head threaded rod 221 apart.

In another embodiment, the first support plate 211 and the second support plate 212 can also be fixedly connected to each other by a threaded support rod. At this time, the positioning among the first plate 211, the second plate 212 and the connecting plate 213 can be realized by locking a positioning nut engaged on the support rod, i.e. replacing the positioned sleeve 214 by the positioning nut.

Figure 6:
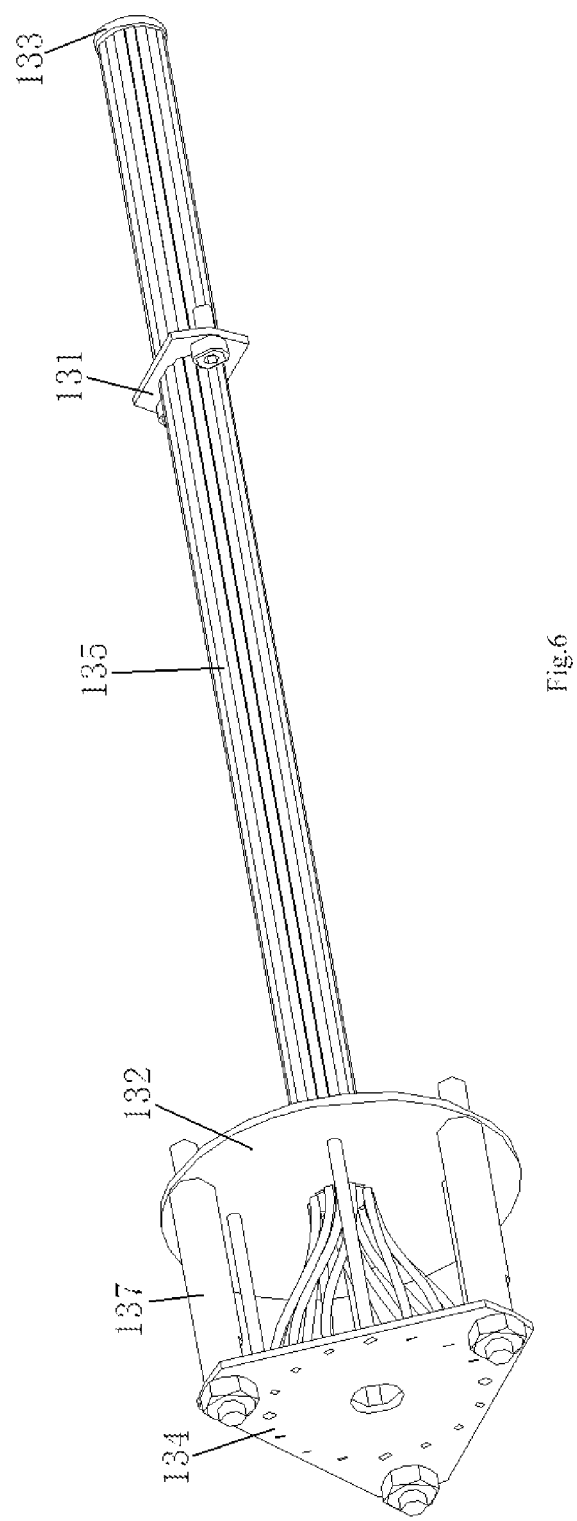
FIG. 6 is a structural diagram of the connecting body (with the second guide channel not shown) according to an embodiment of the present invention.

Furthermore, as shown in FIGS. 5 and 6, the connecting body 13 includes a channel connecting plate 131, a channel support plate 132, a distal fixation plate 133, a proximal structure fixation plate 134, a first guide channel 135 and a second guide channel 136. The channel connecting plate 131 is securely connected to the first support plate 211. The channel support plate 132 is securely connected to the second support plate 212. The proximal structure fixation plate 134 is securely connected to the channel support plate 132 via a connecting post 137. The first guide channel 135 is securely connected at one end to the proximal structure fixation plate 134, and is securely connected at the other end to the distal fixation plate 133 after through the channel support plate 132, the channel connecting plate 131 in sequence; the second distal structural backbones 153 and the proximal structural backbones 123 extend through the first guide channel 135. The second guide channel 136 is provided between the distal fixation plate 133 and the channel connecting plate 131. The first distal structural backbones 143 extend through the second guide channel 136. In a substitute embodiment, the channel support plate 132 and the connecting post 137 can be omitted, then the proximal structure fixation plate 134 can be securely connected to the second support plate 212 directly.

Figure 3:
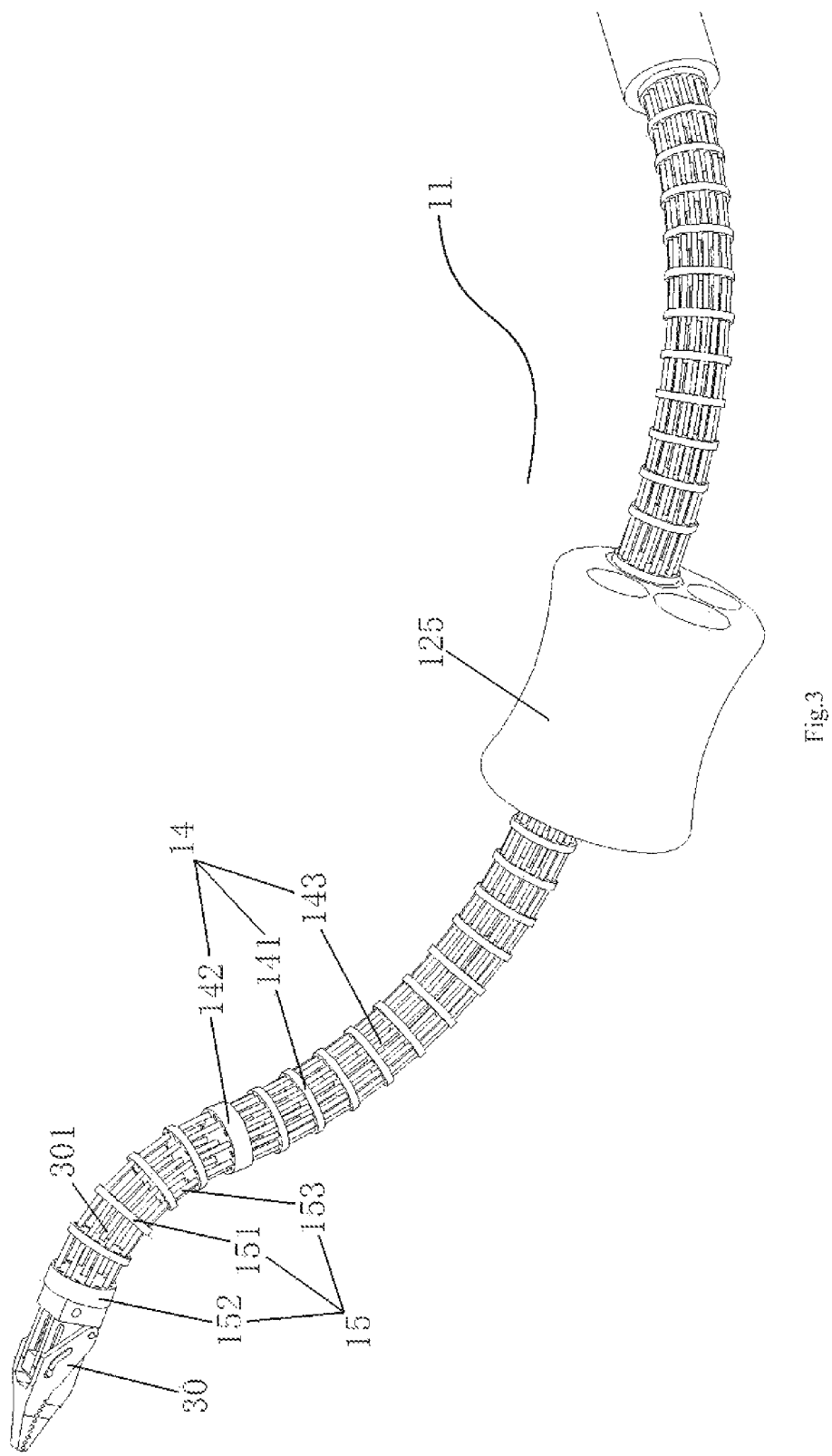
FIG. 3 is a structural diagram of the distal structure according to an embodiment of the present invention.
Figure 4:
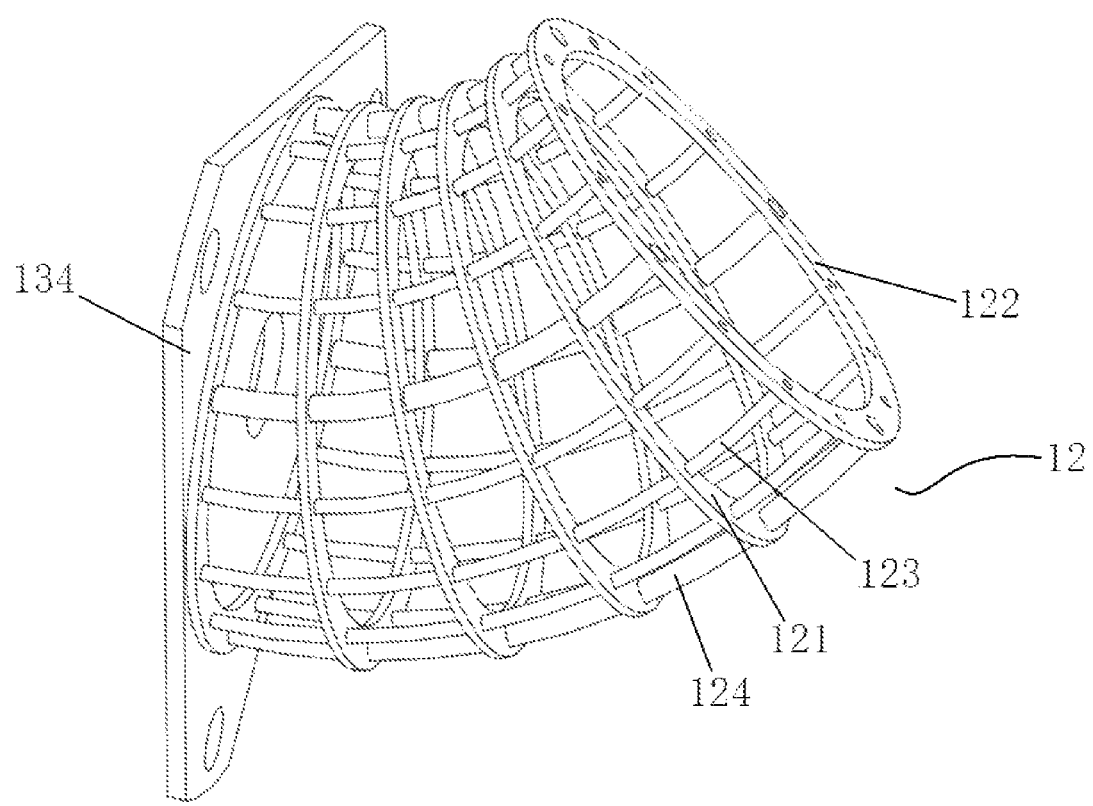
FIG. 4 is a structural diagram of the proximal structure according to an embodiment of the present invention.

Furthermore, as shown in FIG. 3, a surgical end effector 30 is provided at a tip of the second distal segment 15. In the fundamental frame 21, there is provided an end effector driving mechanism, an output end of which is connected to the surgical end effector 30 by a surgical end effector actuation wire 301. As shown in FIG. 5, the end effector driving mechanism includes a screw 303 rotatably provided in the fundamental frame 21, and a sliding block 304 is engaged on the screw 303 and slidably connected to a guide rod 305 fixedly provided in the fundamental frame 21. The sliding block 304 is securely connected to the surgical end effector actuation wire as an output end of the end effector driving mechanism. As the screw 303 rotates in different directions, the sliding block 304 on the screw 303 can linearly move along the guide rod 305 up and down, thus in turn can push and pull the surgical end effector actuation wire 301 to realize open and closing drive for the end surgical end effector 30.

Figure 10:
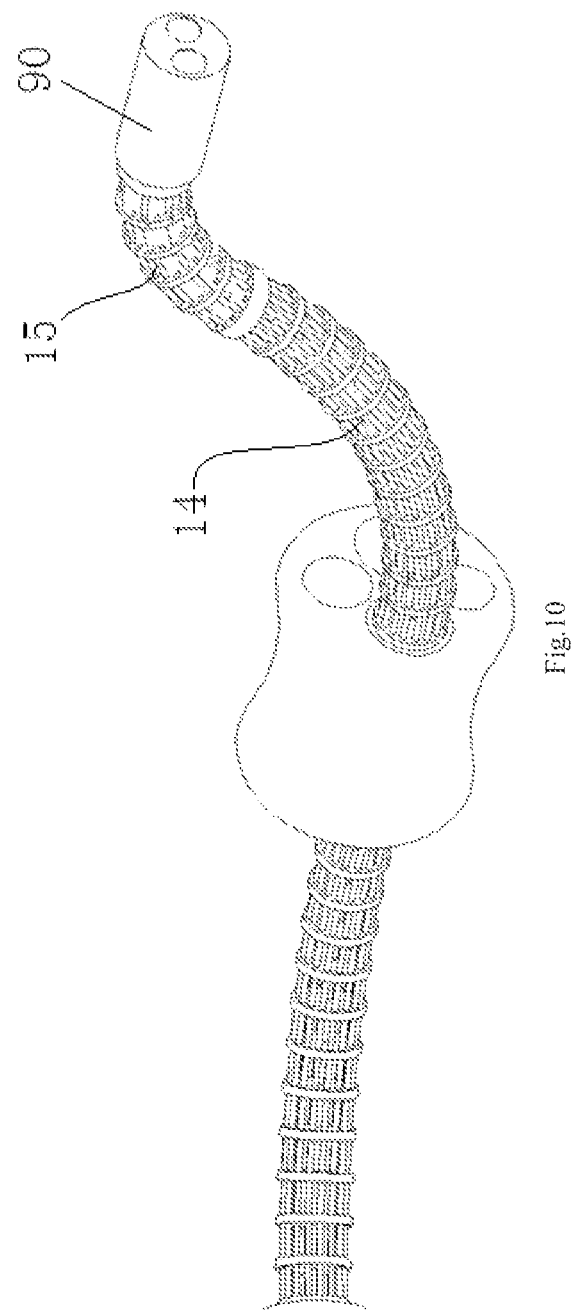
FIG. 10 is a structural diagram of the tip of the distal structure, when connected to a visual illumination module, according to another embodiment of the present invention.
Figure 11:
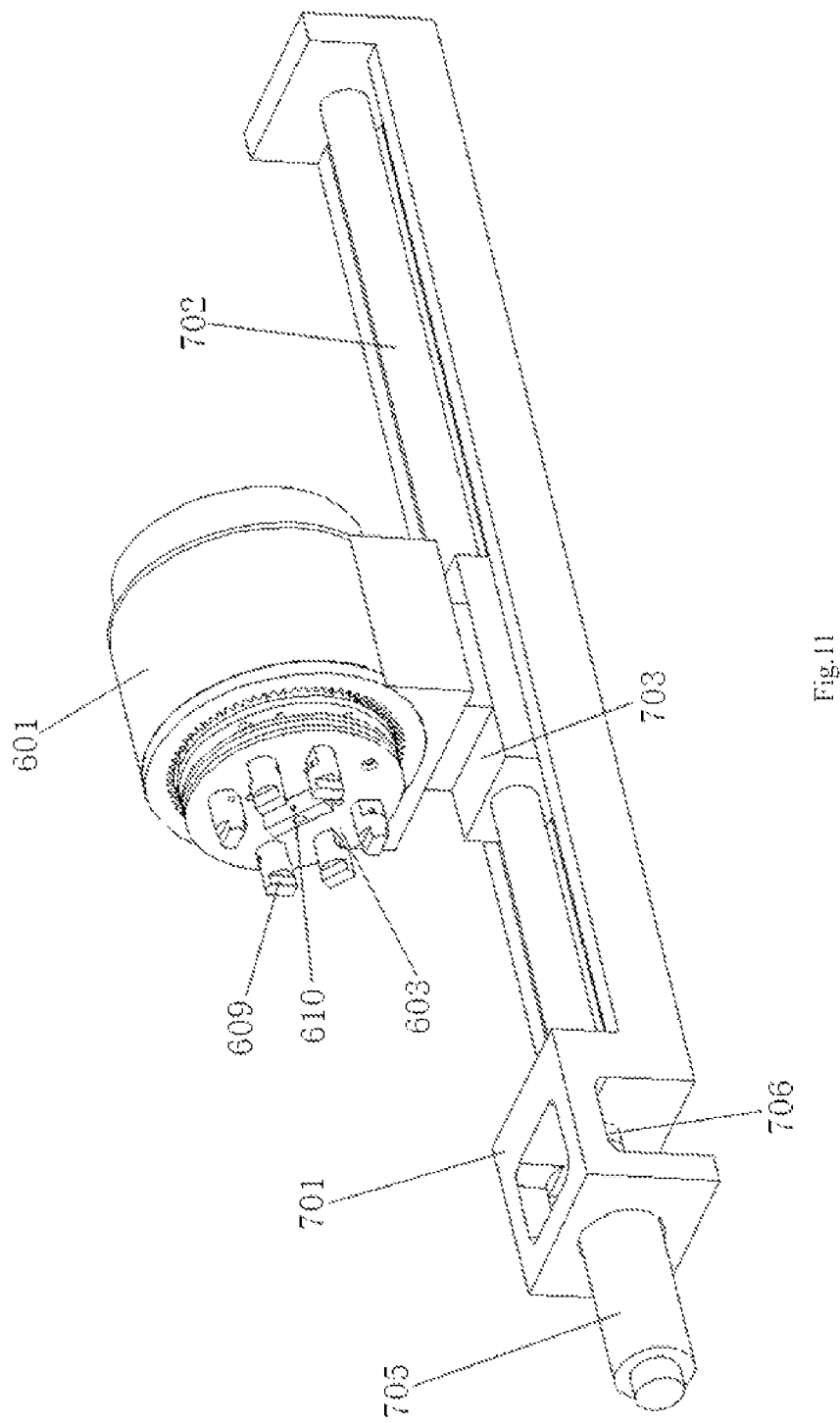
FIG. 11 is a diagram showing connection between a linear actuation module and a multi-motor assembly unit, according to another embodiment of the present invention.
Figure 12:
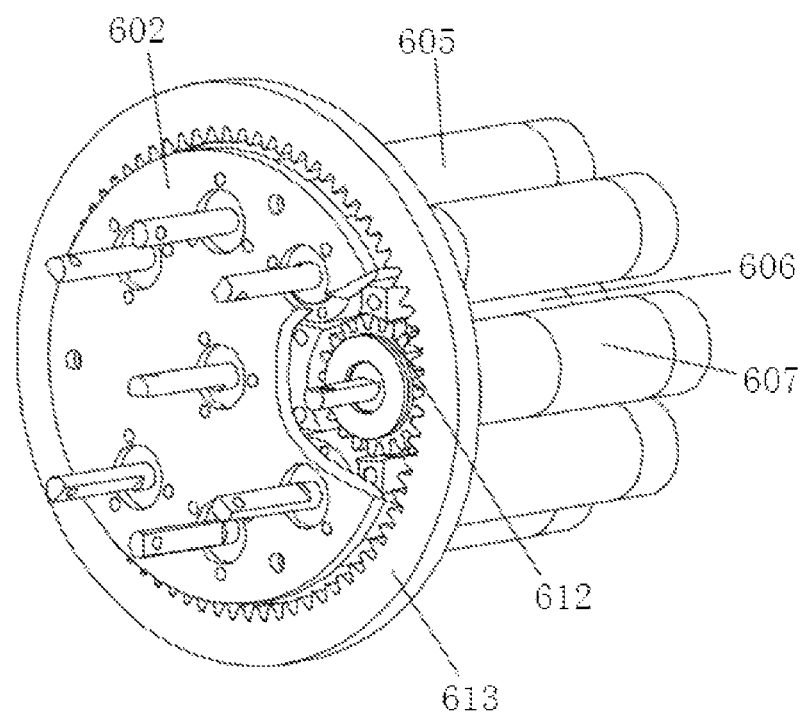
FIG. 12 is a structural diagram of the motor assembly unit according to another embodiment of the present invention, with the cover plate removed.
Figure 13:
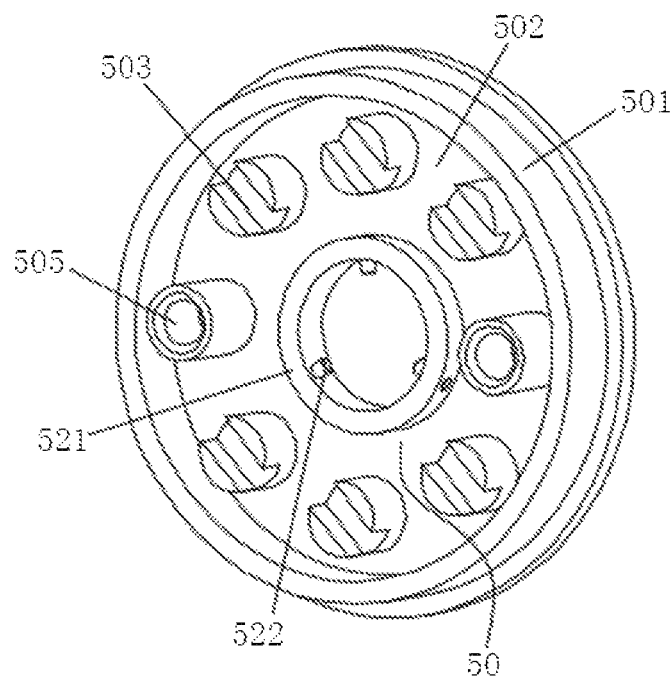
FIG. 13 is a structural diagram of the sterile barrier according to another embodiment of the present invention.
Figure 14:
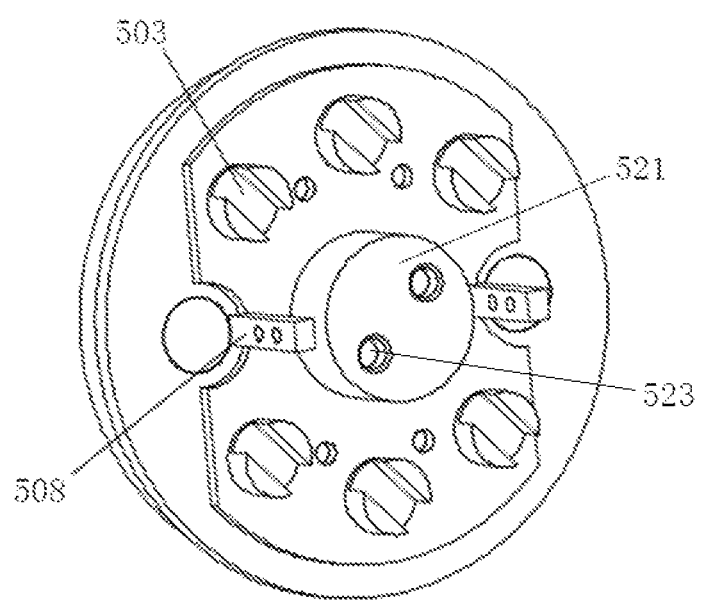
FIG. 14 is a structural diagram in another perspective of the sterile barrier according to another embodiment of the present invention.
Figure 15:
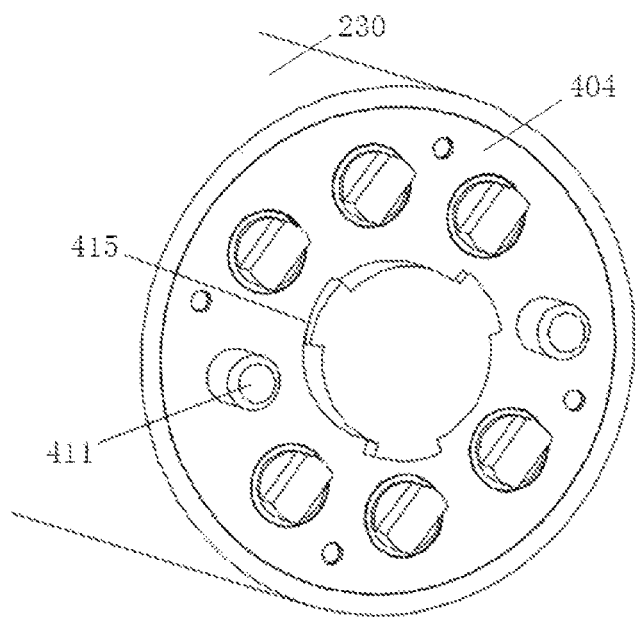
FIG. 15 is a structural diagram of a rear end of the flexible surgical instrument according to another embodiment of the present invention.

As shown in FIG. 3, the surgical end effector 30 located at the tip of the second distal segment 15 can be replaced by other functional end effector, for example the visual illumination module 90 shown in FIG. 10. At this time, a visual processing unit and an illumination control unit can be provided in the fundamental frame 21. The visual processing unit and the illumination control unit can be connected to the visual illumination module 90 by a composite conductor. The posture of the visual illumination module 90 can be adjusted by driving of the distal structure 11, to obtain an real time image of a visual field of the working site.

Further, as shown in FIG. 5, the surgical flexible instrument 10 also includes an elastic connecting mechanism 40. The elastic connecting mechanism 40 includes a joint 401, a coupling male connecter 402, a third support plate 403, a fourth support plate 404 and a spring 405. The third support plate 403 is fixedly connected to the second support plate 212 by a support rod 406. The fourth support plate 404 is fixedly connected to the third support plate 403 by a support rod 407. The joint 401 is slidably connected on the third support plate 403. When the linear motion mechanism 22 shown in FIG. 5 is utilized, the double-head threaded rod 221 or the screw 303 is slidably and non-rotatably connected to one end of the joint 401. When the linear motion mechanism 22 shown in FIG. 9 is utilized, the driving screw 221a or the screw 303 is slidably and non-rotatably connected to one end of the joint 401. The other end of the joint 401 is connected to one end of the coupling male connecter 402. The coupling male connecter 402 is slidably and rotatably mounted on the fourth support plate 404. The spring 405 is sleeved on the coupling male connecter 402. The spring 405 is abut against the third support plate 403 at one end, and fixedly connected to the coupling male connecter 402 at the other end. When the coupling male connecter 402 is approaching axially but not aligned to the coupling female connecter 503 (the coupling female connecter 503 will be described in detail below, and is fixedly connected to the rotating shaft of the driving motor), the coupling female connecter 503 will push the coupling male connecter 402 to move axially, and compress the spring 405. At this time, since the coupling female connecter 503 rotates axially, when it rotates to an extent in which it aligns to the coupling male connecter 402, the spring 405 will spring the coupling male connecter 402 back to restore the position, then the connection between the coupling male connecter and the coupling female connecter is achieved and the rotary motion can be transferred to the screw 303 and the double-head threaded rod 221 or driving screw 221a.

Figure 7:
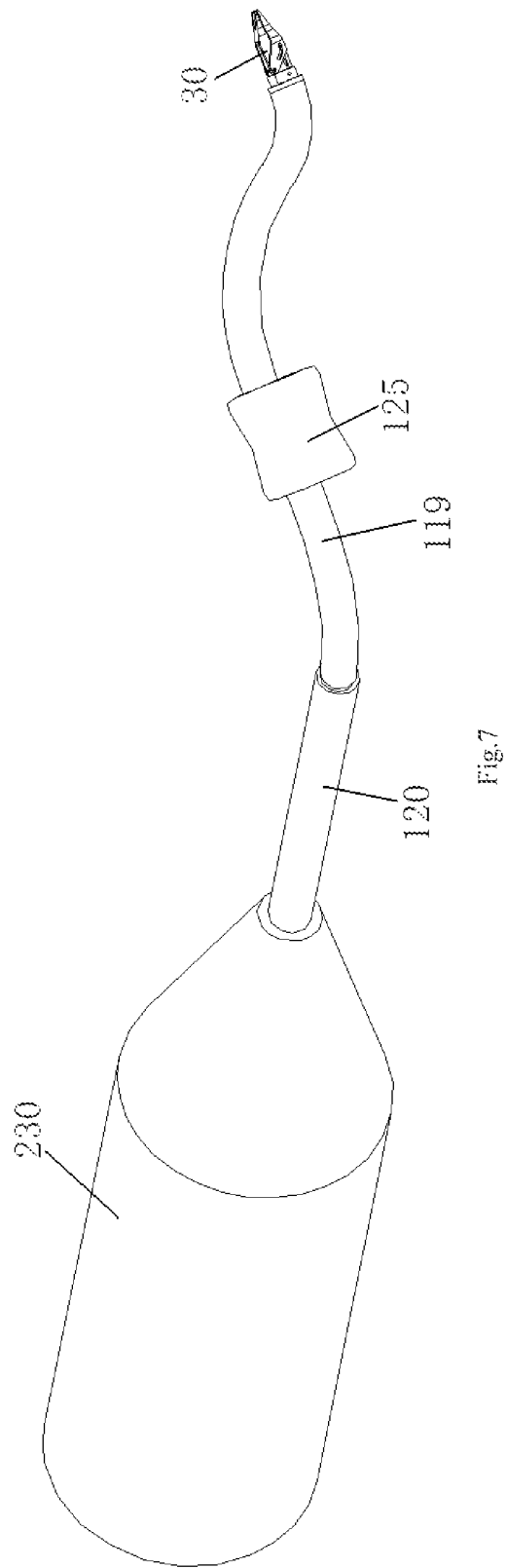
FIG. 7 is a structural diagram of the flexible surgical instrument according to an embodiment of the present invention, with the housing, envelope and the trocar mounted.
Figure 8:
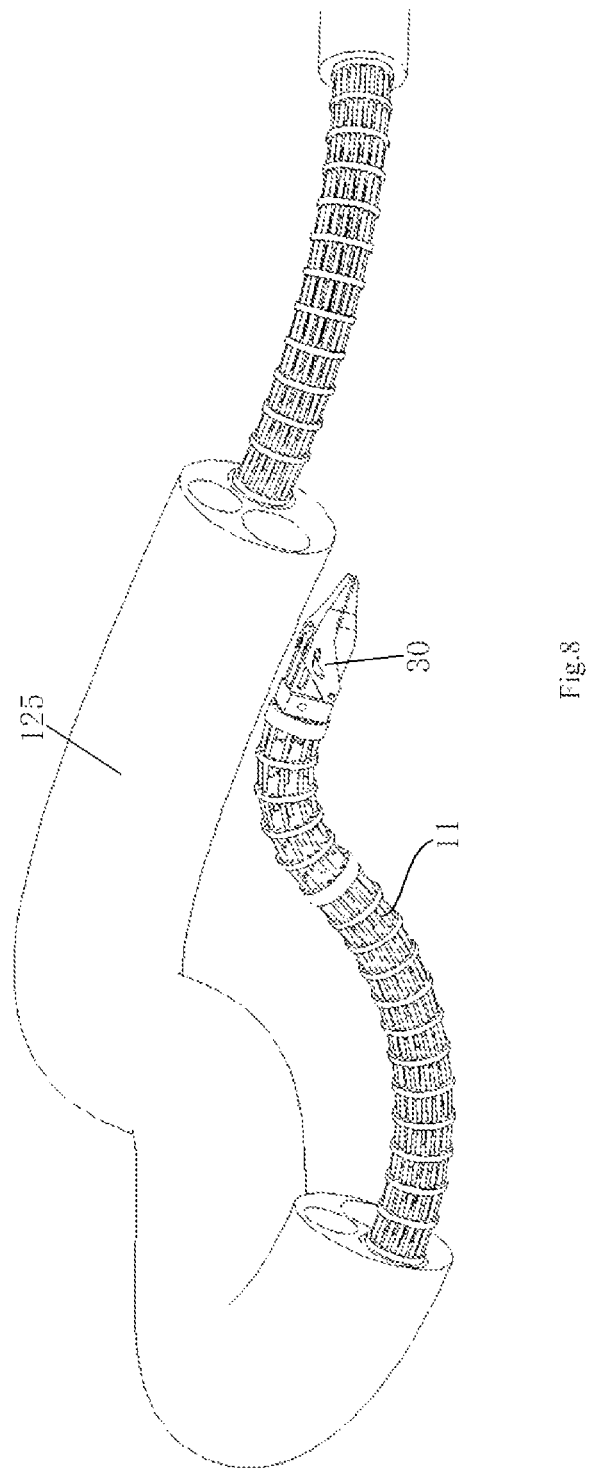
FIG. 8 is a structural diagram of the flexible trocar according to an embodiment of the present invention.

Furthermore, a housing 230 is provided outside the transmission driving unit 20 and the elastic connecting mechanism 40. The first support plate 211 and the second support plate 212 are both securely connected to the housing 230. An envelope 119 is provided outside of the distal structure 11, to improve smoothness of entrance of the distal structure 11 into a natural orifice of human body or a surgical incision. An outer sheath 120 and a trocar 125 can be provided outside the envelop 119. As shown in FIG. 7, in one application, the trocar 125 is secured at a single incision of the abdomen. The distal structure 11 together with the envelop 119, the surgical end effector 30 can freely extend through a through hole on the trocar 125 for passing of the surgical instrument to the surgical site. As shown in FIG. 8, the trocar 125 can be a flexible trocar, so that it can more easily extend into various natural orifice of human body and adaptively change its shape according to the shape of the orifice. One end of the flexible trocar is secured to an inlet of the orifice. The distal structure 11 together with the envelop 119 and the surgical end effector 30 can also freely extend through the through hole on the flexible trocar for passage of the surgical instrument to the surgical site.

Further, as shown in FIGS. 11-15, the multi-motor assembly unit 60 includes a multi-motor assembly housing 601. A motor fixation plate 602 is rotatably connected to the front end of the multi-motor assembly housing 601. A cover plate 603 is securely connected to the front side of the motor fixation plate 602. A plurality of first motors 605, one second motor 606 and one third motor 607 is securely connected at the rear side of the motor fixation plate 602. The output shafts of the first motors 605 extend through the cover plate 603 and are securely connected to the second coupling male connecters 609. The output shaft of the second motor 606 extends through the cover plate 603 and is securely connected to a connecting block 610. An output shaft of the third motor 607 is securely connected with a gear 612. The gear 612 meshes with an internal ring gear 613. The internal ring gear 613 is securely connected to the multi-motor assembly housing 601.

The sterile barrier 50 includes a sterile barrier cover 501, a sterile barrier support plate 502 and a coupling female connecters 503. The coupling female connecters 503 are rotatably provided on the sterile barrier support plate 502, for connecting the coupling male connecters 402 and the second coupling male connecters 609. The sterile barrier cover 501 is rotatably connected at the periphery of the sterile barrier support plate 502. A positioning pin hole 505 is provided at the front side of the sterile barrier support plate 502. A positioning pin 411 for engaging with the positioning pin hole 505 is provided at the rear side of the fourth support plate 404 of the flexible surgical instrument 10. A connecting pin seat 508 is provided at the rear side of the sterile barrier support plate 502. A second connecting pin seat (not shown in the drawings) for connecting to the connecting pin seat 508 is provided at the front side of the cover plate 603 of the multi-motor assembly unit 60. The sterile barrier support plate 502 is further provided with a rapid locking device. The rapid locking device includes a rapid locking body 521 and a locking pin 522. The rapid locking body 521 is roratably connected to the sterile barrier support plate 502. One end of the rapid locking body 521 is of thin wall structure, and the other end thereof is provided with two round holes 523 in an axial direction. The round holes 523 are used for connecting with projecting pins (not shown in the drawings) provided on the connecting block 610 so as to transfer rotation power. The locking pin 522 is circumferentially arranged along the inner wall of the thin wall structure. A helical feature 415 is provided at the rear side of the fourth support plate 404, and in an embodiment, the helical feature 415 is embodied as three lateral wedged protrusions spaced at 120 degree in a circumferential direction of a cylinder at a middle portion of the rear side of the fourth support plate 404. As the rapid locking body 521 rotates to move the locking pin 522 on the helical feature 415, the sterile barrier support plate 502 will be pulled to or pushed away from the fourth support plate 404. When the positioning pin hole 505 aligns and connects with the positioning pin 411, a circumferential position of the coupling male connecter 402 on the flexible surgical instrument 10 completely corresponds to that of the coupling female connecter 503 of the sterile barrier 50. The positioning pin hole 505 and the positioning pin 411 are provided with contacts, for detecting whether the sterile barrier 50 is in lock-on connection with the flexible surgical instrument 10. The rapid locking device is used for achieving a rapid lock-on connection between the flexible surgical instrument 10 and the sterile barrier 50. When the flexible surgical instrument 10 is connected to the sterile barrier 50, the positioning pin 411 of the flexible surgical instrument 10 is aligned and connected to the positioning pin hole 505 in the sterile barrier 50, so that it is guaranteed that the coupling male connecter 402 of the flexible surgical instrument 10 is aligned in position to the coupling female connecter 503 of the sterile barrier 50.

By actuation of the second motor 606, power is transferred through the connecting block 610 to the rapid locking body 521 to rotate it. Then the locking pins 522 embedded in the inner wall of the rapid locking body 521 move along the helical feature 415 of the flexible surgical instrument 10. Thus, the rotation of the rapid locking body 521 results in a tensioning movement of the flexible surgical instrument 10 and the sterile barrier 50 towards each other in the axial direction, and thus the contacts on the positioning pin 411 and contacts on the positioning pin hole 505 gradually approach toward each other. When the contacts of the positioning pin 411 and the contacts of the positioning pin hole 505 contact with each other, a rapid lock-on connection of the flexible surgical instrument 10 with the sterile barrier 50 are realized, and the second motor 606 stops rotating. The first motor 605 is actuated, which drives the coupling female connecter 503 of the sterile barrier 50 to rotate, until it aligns with the coupling male connecter 402 of the flexible surgical instrument 10. When the coupling female connecter 503 aligns with the coupling male connecter 402, the elastic connecting mechanism 40 eject the coupling male connecter 402, then connection between the coupling male connecter 402 and the coupling female connecter 503 is achieved. A sterile film (not shown in the drawings) are connected on the sterile barrier cover 501, which can separate the sterilized portion positioned before the sterile barrier 50, such as the flexible surgical instrument 10, from the portion not sterilized positioned behind the sterile barrier 50, such as the multi-motor assembly unit 60 and the linear actuation module 70, so as to guarantee the implementation of the surgery. After the third motor 607 is actuated, the output shaft thereof rotates and thus rotates the gear 612. The gear 612 will advance in rotation along the circumference of the internal ring gear 613, thus rotating the parts of the multi-motor assembly unit 60, except the multi-motor assembly housing 601 and the internal ring gear 613, as a whole about its own axis, and in turn driving the flexible surgical instrument 10 to rotate about its own axis as a whole, and eventually realizing control of a roll angle of the surgical end effector 30.

Further, the linear actuation module 70 includes a support body 701 with a sliding slot. A lead screw 702 is rotatably provided on the support body 701. A sliding block 703 is sleeved on the lead screw 702, functioning as an output end of the linear actuation module 70. The sliding block 703 is engaged with the lead screw 702 by threads, and is slidably provided in the sliding slot. The support body 701 is provided, at one end, with a fourth motor 705. An output shaft of the fourth motor 705 is securely connected to the lead screw 702 by a coupling 706. The multi-motor assembly housing 601 is securely connected to the sliding block 703. When the output shaft of the fourth motor 705 rotates, the sliding block 703 will linearly move the multi-motor assembly housing 601 along the sliding slot, thus a linear feed motion of the flexible surgical instrument 10 is achieved.

The present invention is described only by the above embodiments, and the structure, providing position and connection of the parts can be varied. Based on the technical solutions of the present invention, the modification or equivalent variations on the individual parts based on the principle of the present invention shall not be excluded from the protective scope of the present invention.

The invention claimed is:

1. A flexible surgical instrument, comprising:
a proximal structure comprising a proximal fixing disk, proximal structural backbones and driving backbones;
a distal structure comprising:
a first distal segment comprising a first distal fixing disk and first distal structural backbones, and
a second distal segment comprising a second distal fixing disk and second distal structural backbones, the proximal structural backbones being securely connected to or the same as the second distal structural backbones; and
a transmission driving unit comprising a plurality of linear motion mechanisms operable to convert a rotary motion input to a linear motion output, the plurality of linear motion mechanisms comprising:
a first linear motion mechanism, an output end of the first linear motion mechanism is connected directly to the first distal structural backbones to bend the first distal segment; and
a second linear motion mechanism, an output end of the second linear motion mechanism is connected to the driving backbones to bend the proximal structure and bend the second distal segment,
wherein each of the plurality of linear motion mechanisms comprises:
a driving screw;
a first pulley coaxially connected to the driving screw;
a second pulley driven by the first pulley;

a driven screw coaxially connected to the second pulley;
a first threaded slider engaged with the driving screw; and
a second threaded slider engaged with the driven screw.

2. The flexible surgical instrument of claim 1, wherein:
a proximal end of each of the proximal structural backbones is securely connected to the proximal fixing disk;
a proximal end of each of the driving backbones is securely connected to the proximal fixing disk;
a distal end of each of the first distal structural backbones is securely connected to the first distal fixing disk; and
a distal end of each of the second distal structural backbones is securely connected to the second distal fixing disk.

3. The flexible surgical instrument of claim 1, wherein each of the second distal structural backbones passes through the first distal segment, and a distal end of each of the second distal structural backbones is securely connected to the second distal fixing disk.

4. The flexible surgical instrument of claim 3, further comprising a functional end effector disposed at a distal end of the second distal segment.

5. The flexible surgical instrument of claim 4, wherein:
the functional end effector comprises a surgical end effector, and
the flexible surgical instrument further comprises:
an effector driving mechanism, an output end of the effector driving mechanism being connected to the surgical end effector by a surgical end effector actuation wire; or
the functional end effector comprises a visual illumination module, and
the flexible surgical instrument further comprises:
a visual processing unit; and
an illumination control unit, and
the visual processing unit and the illumination control unit are capable of being connected to the visual illumination module by a composite conductor.

6. The flexible surgical instrument of claim 1, wherein:
the proximal structure further comprises a proximal spacing disk, the proximal structural backbones pass through the proximal spacing disk;
the first distal structural segment further comprises a first distal spacing disk, the first distal structural backbones pass through the distal spacing disk; and
the second distal structural segment further comprises a second distal spacing disk, the second distal structural backbones pass through the second distal spacing disk.

7. The flexible surgical instrument of claim 1, further comprising a first connecting body comprising:
a proximal structural fixation plate connected to a distal end of the proximal structure;
a distal fixation plate on the proximal side of the first or second distal segment; and
a plurality of first guide channels disposed between the proximal structural fixation plate and the distal fixation plate, and
the second distal structural backbones pass through the plurality of first guide channels.

8. The flexible surgical instrument of claim 7, further comprising a second connecting body comprising:
a channel connecting plate disposed between the proximal structural fixation plate and the distal fixation plate; and
a plurality of second guide channels disposed between the channel connecting plate and the distal fixation plate, and
the first distal structural backbones pass through the plurality of second guide channels.

9. The flexible surgical instrument of claim 1, further comprising an elastic connecting mechanism comprising:
a joint comprising a first joint end slidably connected to the first linear motion mechanism or the second linear motion mechanism;
a coupling comprising a first end connected to a second joint end of the joint;
a joint support plate, the joint slidably connected on the joint support plate;
a coupling support plate, the coupling being slidably and rotatably mounted on the joint support plate; and
a spring sleeved on the coupling, a first end of the spring being connected to the joint support plate and a second end of the spring being connected to the coupling.

10. A flexible surgical instrument system, comprising:
a flexible surgical instrument comprising:
a proximal structure comprising a proximal fixing disk, proximal structural backbones and driving backbones;
a distal structure comprising:
a first distal segment comprising a first distal fixing disk and first distal structural backbones, and
a second distal segment comprising a second distal fixing disk and second distal structural backbones, the proximal structural backbones being securely connected to or the same as the second distal structural backbones; and
a transmission driving unit comprising a plurality of linear motion mechanisms operable to convert a rotary motion input to a linear motion output, the plurality of linear motion mechanisms comprising:
a first linear motion mechanism, an output end of the first linear motion mechanism is connected directly to the first distal structural backbones to bend the first distal segment; and
a second linear motion mechanism, an output end of the second linear motion mechanism is connected to the driving backbones to bend the proximal structure and bend the second distal segment; and
a motor assembly unit operable to drive the transmission driving unit;
wherein each of the plurality of linear motion mechanisms comprises:
a driving screw;
a first pulley coaxially connected to the driving screw;
a second pulley driven by the first pulley;
a driven screw coaxially connected to the second pulley;
a first threaded slider engaged with the driving screw; and
a second threaded slider engaged with the driven screw.

11. The flexible surgical instrument system of claim 10, further comprising a sterile barrier, a first end of the sterile barrier connected to the flexible surgical instrument and a second end of the sterile barrier connected to the motor assembly unit.

12. The flexible surgical instrument system of claim 11, wherein the motor assembly unit comprises:
a motor fixation plate;
a first motor securely mounted on the motor fixation plate;
a first coupling, a first end of the first coupling being connected to an output shaft of the first motor;
the sterile barrier comprises:
a sterile barrier support plate; and a second coupling rotatably disposed at the sterile barrier support plate, a first end of the second coupling being connected to a second end of the first coupling and a second end of the second coupling being connected to the first linear motion mechanism or the second linear motion mechanism.

13. The flexible surgical instrument system of claim 12, wherein the flexible surgical instrument further comprises an elastic connecting mechanism comprising:
a joint comprising a first joint end slidably connected to the first linear motion mechanism or the second linear motion mechanism;
a third coupling comprising a first end connected to a second joint end of the joint;
a joint support plate, the joint slidably being connected on the joint support plate;
a coupling support plate, the third coupling being slidably and rotatably mounted on the joint support plate; and
a spring sleeved on the third coupling and a first end of the spring connected to the joint support plate and a second end of the spring connected to the third coupling.

14. The flexible surgical instrument system of claim 13, wherein:
a positioning pin disposed at the coupling support plate;
a positioning pin hole disposed at the sterile barrier support plate;
when the positioning pin is aligned with the positioning pin hole, the second end of the third coupling is aligned in circumferential with the second end of the second coupling.

15. The flexible surgical instrument system of claim 14, wherein the sterile barrier further comprises:
a locking device comprising a locking body and a plurality of locking pins,
the locking body being rotatably connected to the sterile barrier support plate, a first end of the locking body comprising a thin wall structure and a second end of the locking body being axially disposed with a hole, the plurality of locking pins being circumferentially arranged along an inner wall of the thin wall structure;
a helical feature disposed at the coupling support plate, and when the locking body rotates to drive the plurality of locking pins to move on the helical feature, the coupling support plate is away from or close to the sterile barrier support plate.

16. The flexible surgical instrument system of claim 15, wherein the motor assembly unit further comprises:
a connecting block securely connected to the motor fixation plate; and
a second motor securely mounted on the motor fixation plate, and an output shaft of the second motor securely connected to the connecting block.

17. A flexible surgical instrument, comprising:
a proximal structure comprising a proximal fixing disk, proximal structural backbones and driving backbones;
a distal structure comprising:
a first distal segment comprising a first distal fixing disk and first distal structural backbones, and
a second distal segment comprising a second distal fixing disk and second distal structural backbones, the proximal structural backbones being securely connected to or the same as the second distal structural backbones; and
a transmission driving unit comprising a plurality of linear motion mechanisms operable to convert a rotary motion input to a linear motion output, the plurality of linear motion mechanisms comprising:
a first linear motion mechanism, an output end of the first linear motion mechanism is connected directly to the first distal structural backbones to bend the first distal segment; and
a second linear motion mechanism, an output end of the second linear motion mechanism is connected to the driving backbones to bend the proximal structure and bend the second distal segment;
wherein the first linear motion mechanism comprises:
a first double-head threaded rod;
a first threaded slider screwed to a first threaded section of the first double-head rod; and
a second threaded slider screwed to a second threaded section of the first double-head rod, and
the first threaded slider and the second threaded slider are connected to a pair of the first distal structural backbones.

18. The flexible surgical instrument of claim 17, wherein the second linear motion mechanism comprises:
a second double-head threaded rod;
a third threaded slider screwed to a first threaded section of the second double-head rod; and
a fourth threaded slider screwed to a second threaded section of the second double-head rod, and
the third threaded slider and the fourth threaded slider are connected to a pair of the driving backbones.

19. The flexible surgical instrument of claim 17, wherein:
a proximal end of each of the proximal structural backbones is securely connected to the proximal fixing disk;
a proximal end of each of the driving backbones is securely connected to the proximal fixing disk;
a distal end of each of the first distal structural backbones is securely connected to the first distal fixing disk; and
a distal end of each of the second distal structural backbones is securely connected to the second distal fixing disk.

20. The flexible surgical instrument of claim 17, wherein each of the second distal structural backbones passes through the first distal segment, and a distal end of each of the second distal structural backbones is securely connected to the second distal fixing disk.

21. The flexible surgical instrument of claim 20, further comprising a functional end effector disposed at a distal end of the second distal segment.

22. The flexible surgical instrument of claim 21, wherein:
the functional end effector comprises a surgical end effector, and
the flexible surgical instrument further comprises:
an effector driving mechanism, an output end of the effector driving mechanism being connected to the surgical end effector by a surgical end effector actuation wire; or
the functional end effector comprises a visual illumination module, and
the flexible surgical instrument further comprises:
a visual processing unit; and
an illumination control unit, and
the visual processing unit and the illumination control unit are capable of being connected to the visual illumination module by a composite conductor.

23. The flexible surgical instrument of claim 17, wherein:
the proximal structure further comprises a proximal spacing disk, the proximal structural backbones pass through the proximal spacing disk;
the first distal structural segment further comprises a first distal spacing disk, the first distal structural backbones pass through the distal spacing disk; and the second distal structural segment further comprises a second distal spacing disk, the second distal structural backbones pass through the second distal spacing disk.

24. The flexible surgical instrument of claim 17, further comprising a first connecting body comprising:
a proximal structural fixation plate connected to a distal end of the proximal structure;
a distal fixation plate on the proximal side of the first or second distal segment; and
a plurality of first guide channels disposed between the proximal structural fixation plate and the distal fixation plate, and
the second distal structural backbones pass through the plurality of first guide channels.

25. The flexible surgical instrument of claim 24, further comprising a second connecting body comprising:
a channel connecting plate disposed between the proximal structural fixation plate and the distal fixation plate; and
a plurality of second guide channels disposed between the channel connecting plate and the distal fixation plate, and
the first distal structural backbones pass through the plurality of second guide channels.

26. The flexible surgical instrument of claim 17, further comprising an elastic connecting mechanism comprising:
a joint comprising a first joint end slidably connected to the first linear motion mechanism or the second linear motion mechanism;
a coupling comprising a first end connected to a second joint end of the joint;
a joint support plate, the joint slidably connected on the joint support plate;
a coupling support plate, the coupling being slidably and rotatably mounted on the joint support plate; and
a spring sleeved on the coupling, a first end of the spring being connected to the joint support plate and a second end of the spring being connected to the coupling.

27. A flexible surgical instrument system, comprising:
a flexible surgical instrument comprising:
a proximal structure comprising a proximal fixing disk, proximal structural backbones and driving backbones;
a distal structure comprising:
a first distal segment comprising a first distal fixing disk and first distal structural backbones, and
a second distal segment comprising a second distal fixing disk and second distal structural backbones, the proximal structural backbones being securely connected to or the same as the second distal structural backbones; and
a transmission driving unit comprising a plurality of linear motion mechanisms operable to convert a rotary motion input to a linear motion output, the plurality of linear motion mechanisms comprising:
a first linear motion mechanism, an output end of the first linear motion mechanism is connected directly to the first distal structural backbones to bend the first distal segment; and
a second linear motion mechanism, an output end of the second linear motion mechanism is connected to the driving backbones to bend the proximal structure and bend the second distal segment; and
a motor assembly unit operable to drive the transmission driving unit;
wherein each of the plurality of linear motion mechanisms comprises:
a first double-head threaded rod;
a first threaded slider screwed to a first threaded section of the first double-head rod; and
a second threaded slider screwed to a second threaded section of the first double-head rod, and
the first threaded slider and the second threaded slider are connected to a pair of the first distal structural backbones.

28. The flexible surgical instrument system of claim 27, wherein the second linear motion mechanism comprises:
a second double-head threaded rod;
a third threaded slider screwed to a first threaded section of the second double-head rod; and
a fourth threaded slider screwed to a second threaded section of the second double-head rod, and
the third threaded slider and the fourth threaded slider are connected to a pair of the driving backbones.

29. The flexible surgical instrument system of claim 27, further comprising a sterile barrier, a first end of the sterile barrier connected to the flexible surgical instrument and a second end of the sterile barrier connected to the motor assembly unit.

30. The flexible surgical instrument system of claim 29, wherein the motor assembly unit comprises:
a motor fixation plate;
a first motor securely mounted on the motor fixation plate;
a first coupling, a first end of the first coupling being connected to an output shaft of the first motor;
the sterile barrier comprises:
a sterile barrier support plate; and
a second coupling rotatably disposed at the sterile barrier support plate, a first end of the second coupling being connected to a second end of the first coupling and a second end of the second coupling being connected to the first linear motion mechanism or the second linear motion mechanism.

31. The flexible surgical instrument system of claim 30, wherein the flexible surgical instrument further comprises an elastic connecting mechanism comprising:
a joint comprising a first joint end slidably connected to the first linear motion mechanism or the second linear motion mechanism;
a third coupling comprising a first end connected to a second joint end of the joint;
a joint support plate, the joint slidably being connected on the joint support plate;
a coupling support plate, the third coupling being slidably and rotatably mounted on the joint support plate; and
a spring sleeved on the third coupling and a first end of the spring connected to the joint support plate and a second end of the spring connected to the third coupling.

32. The flexible surgical instrument system of claim 31, wherein:
a positioning pin disposed at the coupling support plate;
a positioning pin hole disposed at the sterile barrier support plate;
when the positioning pin is aligned with the positioning pin hole, the second end of the third coupling is aligned in circumferential with the second end of the second coupling.

33. The flexible surgical instrument system of claim 32, wherein the sterile barrier further comprises:
a locking device comprising a locking body and a plurality of locking pins,
the locking body being rotatably connected to the sterile barrier support plate, a first end of the locking body comprising a thin wall structure and a second end of the locking body being axially disposed with a hole, the plurality of locking pins being circumferentially arranged along an inner wall of the thin wall structure;

a helical feature disposed at the coupling support plate, and when the locking body rotates to drive the plurality of locking pins to move on the helical feature, the coupling support plate is away from or close to the sterile barrier support plate.

34. The flexible surgical instrument system of claim 33, wherein the motor assembly unit further comprises:

a connecting block securely connected to the motor fixation plate; and a second motor securely mounted on the motor fixation plate, and an output shaft of the second motor securely connected to the connecting block.

* * * * *